US008457710B2

(12) United States Patent
Biglieri et al.

(10) Patent No.: US 8,457,710 B2
(45) Date of Patent: Jun. 4, 2013

(54) DIAGNOSTIC IMAGING METHOD AND APPARATUS FOR THE ANATOMICAL REGION OF THE PELVIC FLOOR

(75) Inventors: Eugenio Biglieri, Masio (IT); Luigi Satragno, Genova (IT)

(73) Assignee: Esaote S.p.A., Milan (IT)

( * ) Notice: Subject to any disclaimer, the term of this patent is extended or adjusted under 35 U.S.C. 154(b) by 1538 days.

(21) Appl. No.: 11/873,548

(22) Filed: Oct. 17, 2007

(65) Prior Publication Data

US 2008/0139921 A1 Jun. 12, 2008

(30) Foreign Application Priority Data

Oct. 19, 2006 (EP) .................................. 06425722

(51) Int. Cl.
*A61B 5/05* (2006.01)

(52) U.S. Cl.
USPC ............... 600/410; 600/407; 600/411; 703/2; 703/11

(58) Field of Classification Search
USPC .......................... 600/407, 410, 411; 703/2, 11
See application file for complete search history.

(56) References Cited

U.S. PATENT DOCUMENTS

| 4,964,153 A | 10/1990 | Lassiter |
| 5,008,624 A | 4/1991 | Yoshida |
| 5,329,234 A | 7/1994 | Burton |
| 5,349,956 A | 9/1994 | Bonutti |
| 5,594,337 A | 1/1997 | Boskamp |
| 6,738,499 B1 | 5/2004 | Doi et al. |
| 7,937,249 B2 * | 5/2011 | Osborn et al. .................... 703/2 |
| 2002/0123681 A1 | 9/2002 | Zuk et al. |

(Continued)

FOREIGN PATENT DOCUMENTS

| DE | 103 12 193 | 9/2004 |
| EP | 1 530 162 | 5/2005 |
| JP | 2000-139872 | 5/2000 |
| WO | WO 2006/007876 | 1/2006 |

OTHER PUBLICATIONS

Fletcher et al., "Magnetic Resonance Imaging of Anatomic and Dynamic Defects of the Pelvic Floor in Defecatory Disorders" The American Journal of Gastroenterology, 2003, vol. 98, No. 2, pp. 399-411.

(Continued)

*Primary Examiner* — Tse Chen
*Assistant Examiner* — Baisakhi Roy
(74) *Attorney, Agent, or Firm* — Buchanan Ingersoll & Rooney PC

(57) ABSTRACT

A method for determining information for a diagnosis of pathologic conditions of the anatomical region of the pelvic floor by MRI imaging includes acquiring a sequence of MRI images along one or more predetermined section planes or inside a predetermined three-dimensional area, which planes intersect or which three-dimensional area contains at least a part of the pelvic floor. The image sequence is acquired for a time interval coinciding with or including at least a part of the length of the physiological process evacuating natural solids or liquids carried out on the basis both of a natural stimulation and an induced stimulation or during a simulation of physiological processes evacuating solids or liquids by introducing foreign bodies or substances simulating natural products. The method further includes generating a film of the cinematographic type by using as individual frames one or more images of the sequence and displaying the film for visually verifying the dynamic-morphologic behavior of organs of the pelvic floor.

11 Claims, 14 Drawing Sheets

U.S. PATENT DOCUMENTS

| | | |
|---|---|---|
| 2003/0174873 A1 | 9/2003 | Giger et al. |
| 2004/0147840 A1 | 7/2004 | Duggirala et al. |
| 2005/0187459 A1 | 8/2005 | Trequattrini et al. |
| 2006/0047195 A1 | 3/2006 | Shen |
| 2006/0153816 A1* | 7/2006 | Brown et al. ............... 424/93.7 |
| 2007/0015994 A1* | 1/2007 | Hong et al. ................ 600/407 |
| 2007/0016391 A1* | 1/2007 | Minoguchi et al. ............ 703/11 |
| 2007/0027667 A1* | 2/2007 | Osborn et al. ................ 703/11 |

OTHER PUBLICATIONS

Kester et al., "Value of Express $T_2$-Weighted Pelvic MRI in the Preoperative Evaluation of Severe Pelvic Floor Prolapse: A Prospective Study" Adult Urology, 2003, vol. 61, No. 6, pp. 1135-1139.

Perez et al., "Dynamic Magnetic Resonance Imaging of the Female Pelvis: Radio-Anatomy and Pathologic Applications. Preliminary Results" Surgical and Radiologic Anatomy, 1999, vol. 21, No. 2, pp. 133-138.

Singh et al., "Three-Dimensional Magnetic Resonance Imaging Assessment of Levator Ani Morphologic Features in Different Grades of Prolapse" American Journal of Obstetrics and Gynecology, 2003, vol. 188, No. 4, pp. 910-915.

Verhey et al., "Non-Rigid Registration of a 3D Ultrasound and a MR Image Data Set of the Female Pelvic Floor Using a Biomechanical Model" Biomedical Engineering Online, 2005, vol. 4, No. 1, pp. 1-8.

European Search Report in Application No. 06425722.3-1265/1913869 dated Nov. 6, 2008.

\* cited by examiner

DIAGNOSTIC IMAGING METHOD AND APPARATUS FOR THE ANATOMICAL REGION OF THE PELVIC FLOOR

BACKGROUND

The present invention relates to a diagnostic imaging method and apparatus for the anatomical region of the pelvic floor.

Diseases involving the pelvic floor are highly increasing in western countries due to different reasons. As the years go by a percentage of people between 10 and 41% are expected to have troubles related to urinary incontinence, vaginal and/or rectal prolapses or other diseases involving structures composing the pelvic floor. It is clear that said diseases will have a considerable social, psychological and obviously economic effect.

In the medical field the concept of pelvic floor intended as a single functional unit is established. Various specialists that treat diseases involving the pelvic area, such as urologists, gynaecologists, surgeons and coloproctologists have abandoned the conventional distinction between anterior, middle and posterior compartments. It is become clear that the trouble of each segment of the pelvic floor is always associated to different disease degrees of other systems constituting it. As a consequence during the same operating session it is often necessary to perform combined urologic, gynaecological and rectalcolon corrective/reconstructive operations. It has been proved that the sequential treatment of various troubles of the pelvic floor during the same operating session does not lead to an increase in the mortality and it has the further advantage of reducing the length of time the patient is obliged to stay in hospital and the time for the functional recovery.

Devices for acquiring morpho-functional images having the objective of carrying out medical diagnosis are known, particularly not invasive or little invasive imaging devices such as ultrasound apparati or magnetic resonance apparati.

Different kinds of nuclear magnetic resonance apparati are known. A type of apparatus called "total body" has a magnetic structure defining a cavity housing the patient with such a dimension to house the whole body of the patient or a large part thereof. Therefore these apparati are large and poles generating the magnetic field both of the permanent magnet type and of the resistive or superconductive type, generate magnetic fields having a great intensity. The cost of these apparati is high and their installation is complex since they need rooms that have to be large and above all intended to support their considerable weight.

A second type of apparatus so called "dedicated" type comprises magnetic structures of the U-shaped, C-shaped or annular type having such a dimension to be adapted to the examination of some anatomical regions or parts of the patient body and generally they are the head, shoulder or backbone. Generally dedicated apparati are made considering needs as regards dimensions of the cavity defined by the magnetic structure with reference to various parts of the body to be housed in the cavity. Such need often requires these magnetic structures to be combined with structures of the examination table or patient supporting table movably connected to the magnetic structure. This type of apparati has the advantage of requiring magnetic fields having a small intensity and so it allows magnetic structure to be small and not much heavy.

The apparati of the so called "dedicated" type are widely used in the orthopedical and rheumatologic field. The possibility of manufacturing apparati with a smaller size, weight and cost guaranteeing such a magnetic field intensity that diagnostic images are obtained has allows the diffusion and the use of resonance by surgeries and small professional persons even for studying diseases that conventionally are diagnosed on the base of clinical data or by conventional, expensive and bulky apparati, such as radiological apparati.

The spreading of MRI dedicated apparati has allowed to obtain an optimal cost-advantage ratio above all when carrying out muscle skeletal examinations.

After MRI dedicated systems for orthopedy and rheumatology the need to develop MRI systems for carrying out morphofunctional analyses has developed as regards other diseases compromising functional capacities of the patient.

Methods of diagnosis aided by the computer are known, so called CAD computer aided diagnosis, involving the processing of diagnostic images such to highlight shapes and objects in images and to obtain information about the type of the highlighted object.

In order to obtain qualitative and/or quantitative information from images about a predetermined object or about a particular anatomical region, available computers use quite complex algorithms that force the specialist dealing with the treatment of a particular disease to send files relevant to the image or image series to a specialized institute that will process them then providing desired data that will allow the specialist to go on in treating the disease.

This system will lead to an increase of costs and time for treating the patient considerably postponing the starting of the therapy since it involves an exchange of information between the personnel assigned to acquiring images, personnel assigned to processing images and the doctor evaluating images and data obtained by the processing in order to have a right therapy.

Moreover since the method for conventionally processing images involves the interaction of data provided by the work of different specialized persons, it interferes with the possibility of having files of data and diagnostic images of the same patient upon which the processing of data recently acquired can be based.

A further drawback is that CAD-based processing systems work on static images and so are not useful for the dynamic functional in-depth study of those diseases involving an anatomical region in the dynamic condition i.e. they do not allow to analyse and to compare the body part under examination directly during its operation with filed data and images.

OBJECTS AND SUMMARY

Therefore on the basis of such observations it is clear the importance of manufacturing a nuclear magnetic resonance imaging apparatus specific for the anatomical region in question, i.e. the pelvic floor considered in its wholeness, and to develop methods for processing obtained images in order to quickly and completely identify the most precocious trouble phases of the structures composing the pelvic floor such to apply in good time the most right medical-surgical therapies.

An object is to provide a method for determining information helping the diagnosis of pathologic conditions of the anatomical region of the pelvic floor by acquiring and processing MRI images by a device comprising a MRI apparatus dedicated to the acquisition of images of the pelvic floor such that the not invasive study in vivo in the resting condition and in dynamic evacuation condition of the pelvic floor is possible, particularly of the bladder, rectum and other structures present in the anatomical region of the pelvis.

Moreover a further aim is to provide a device integrating means processing images for the dynamic study of the anatomical region by means acquiring them such to combine the medical examination carrying out and a management of images that in the whole are not expensive, with the possibility of quickly and completely identifying most precocious trouble phases and so of preparing the most right medical-surgical therapies.

The disclosed embodiment achieve the above aims by a method providing to acquire a sequence of MRI images, on one or more predetermined section planes or inside a predetermined three-dimensional area, which planes intersect and/or which three-dimensional area contains at least a part of the pelvic floor, for a time interval coinciding with or comprising at least a part of the length of the physiological process evacuating natural solids and/or liquids carried out on the basis both of a natural stimulation and an induced stimulation or during a simulation of physiological processes evacuating solids or liquids by introducing foreign bodies or substances simulating natural products. Said images are used to generate a film of the cinematographic type by using as individual frames one or more images of the MRI sequence for example in the known cineRM mode and the film is displayed on a screen for visually verifying the dynamic-morphologic behaviour of organs and particularly of the pelvic floor.

This method for processing MRI images helps the physician to precociously diagnose the presence of a possible pathologic condition since it allows to obtain from the image sequence not only morphologic information but also functional data of analysed anatomical structures.

The analysis of diseases of the pelvic floor is a typically functional analysis and it requires the development of "real time" sequences having an appropriate contrast and resolution. Therefore the diagnosis needs a basic morphologic analysis having the objective of defining structures of the pelvic floor and of highlighting possible pathologic conditions followed by the functional analysis that is carried out by "real time" scans repeated in time for monitoring the evolution of structures when performing evacuation and micturition functions. Acquired images that are suitably edited as CINE RM allow to analyse the function of the pelvic floor structures under optimal conditions for the physician since the generation of the film and/or the processing of the image sequence occurs in real time that is during or immediately after the acquisition of said images.

CINE RM film prepared according to the method object of the present invention, is not only examined by medical personnel on a screen for visually verifying the dynamic-morphologic behaviour of pelvic floor organs but it is subjected to various processing steps for analysing main structures and for better highlighting pathologic conditions with parameters as objective as possible.

Said processing steps comprise the analysis of MRI signals and of image data as regards contrast and the identification of image regions in the form of subsets of pixels or voxels corresponding to the representation of an object or a structure provided in the three-dimensional area of which the image has been acquired and/or intersected by the scanning plane, and of the recognition of said objects reproduced in the image as regards their morphology and/or their functional meaning. This segmentation process allows to determine shapes and dimensions of anatomical parts, tissues and/or organs and to detect their functional behaviour, particularly it allows to determine the volume of the bladder in the full, empty and/or partially empty condition and/or the volume of the sphincter under various functional conditions. According to an improvement of the present invention these dimensions and/or morphologic parameters are compared with corresponding dimensions and/or morphologic parameters of the same organs obtained by a database of known clinical cases further aiming at creating a staging of the disease condition in order to allow the monitoring during the therapeutic and/or surgical treatment and the subsequent rehabilitation.

In combination with segmentation steps it is possible to further provide the step generating a virtual image reconstructed on the basis of image data processed by means of the segmentation, such as rendering steps possibly combined with morphing and/or smoothing steps by which virtual image sequences are obtained by image sequences subjected to segmentation, wherein various recognized objects are visually represented in order to be different one from the other and to highlight the dynamic behaviour of objects within the sequence.

Moreover object is a diagnostic device allowing to carry out the above diagnosis method, i.e. a device for the morphofunctional diagnosis of the pelvic floor comprising at least an apparatus for acquiring images of the pelvic floor anatomical region by nuclear magnetic resonance, means for generating a film of the cinematographic type by using as individual frames one or more images of the MRI sequence, means for processing images wherein the apparatus and said means generating the film and/or processing means are integrated within the same diagnostic device.

By integrating means for acquiring, generating and displaying MRI images with means generating a film of the cinematographic type and means with CAD functionality for processing images, the invention allows to change the magnetic resonance into a "gold standard" diagnostic investigation method for examining the pelvic floor since said device allows to accurately reproduce the topography taken by the bladder, rectum and all other structures of the pelvic floor under "vivo resting" and "dynamic evacuation" conditions.

An apparatus, comprised in the device described above, is provided for acquiring images of the pelvic floor anatomical region by the fact that the detecting cavity has such a shape and size allowing to receive at least a part of the body under examination, particularly the anatomical region of the pelvis in the seated position and/or upright position.

By means of this new dedicated apparatus it is possible to carry out a functional dynamic in-depth study of all diseases of the pelvic floor structures without using conventional methods using ionizing radiations, such as cystography, cystomanometry, hysterosalpingography, defecography, and thus avoiding serious problems about the radiation protection related to their use.

For examining the pelvic floor in the seated position the MRI apparatus object of the present invention has poles vertically placed so that means for positioning the patient can be inside the detecting cavity allowing the patient to carry out evacuation or micturition function when images are acquired. Said positioning means are a safe support for the patient and at the same time are compatible with the magnetic field and with radiofrequency fields, there being made of not magnetic and/or not metallic materials.

Positioning means can be composed of a chair element like an annular or semi-annular shaped toilet bowl and made of such a material that does not interfere with image acquisition, particularly made of electromagnetically transparent material. In order to guarantee a perfect cleanliness and hygiene said element is coupled to easy removable containers guaranteeing the containment and the simple removal of physiological liquids and solids.

In order to obtain the acquisition of the maximum signal, the coil dedicated to the analysis of the pelvic floor both under static conditions, for the morphologic examination, and under dynamic conditions, for the analysis in real time of the evacuation and micturition process, is integrated at least partially in the support for keeping the patient in the seated position in order to adapt itself to the part under examination.

Therefore the apparatus for acquiring images is dedicated to the acquisition of MRI images of the pelvis region in conditions superimposable to the physiological evacuation condition, particularly with the patient in the seated position in order to accurately reproduce the topography taken by the bladder, rectum and all other structures of the pelvic floor under vivo resting and dynamic evacuation conditions. In said MRI apparatus means for generating the film and processing means with CAD functionality work in sinergy for the in-depth dynamic analysis of all diseases of said structures.

The magnetic structure of the apparatus has a quite small size also as regards the magnetic field. Moreover since means for controlling the MRI apparatus, for acquiring data, for processing images can be as a combination of programs executed by a PC or the like, the device object of the present invention in the whole has a small size and weight and so it is easy and quick to be installed.

BRIEF DESCRIPTION OF THE DRAWINGS

Characteristics of the present invention and advantages deriving therefrom will be more clear from the following description of some embodiments with reference to annexed drawing wherein.

DETAILED DESCRIPTION OF THE PREFERRED EMBODIMENTS

Figure 6:
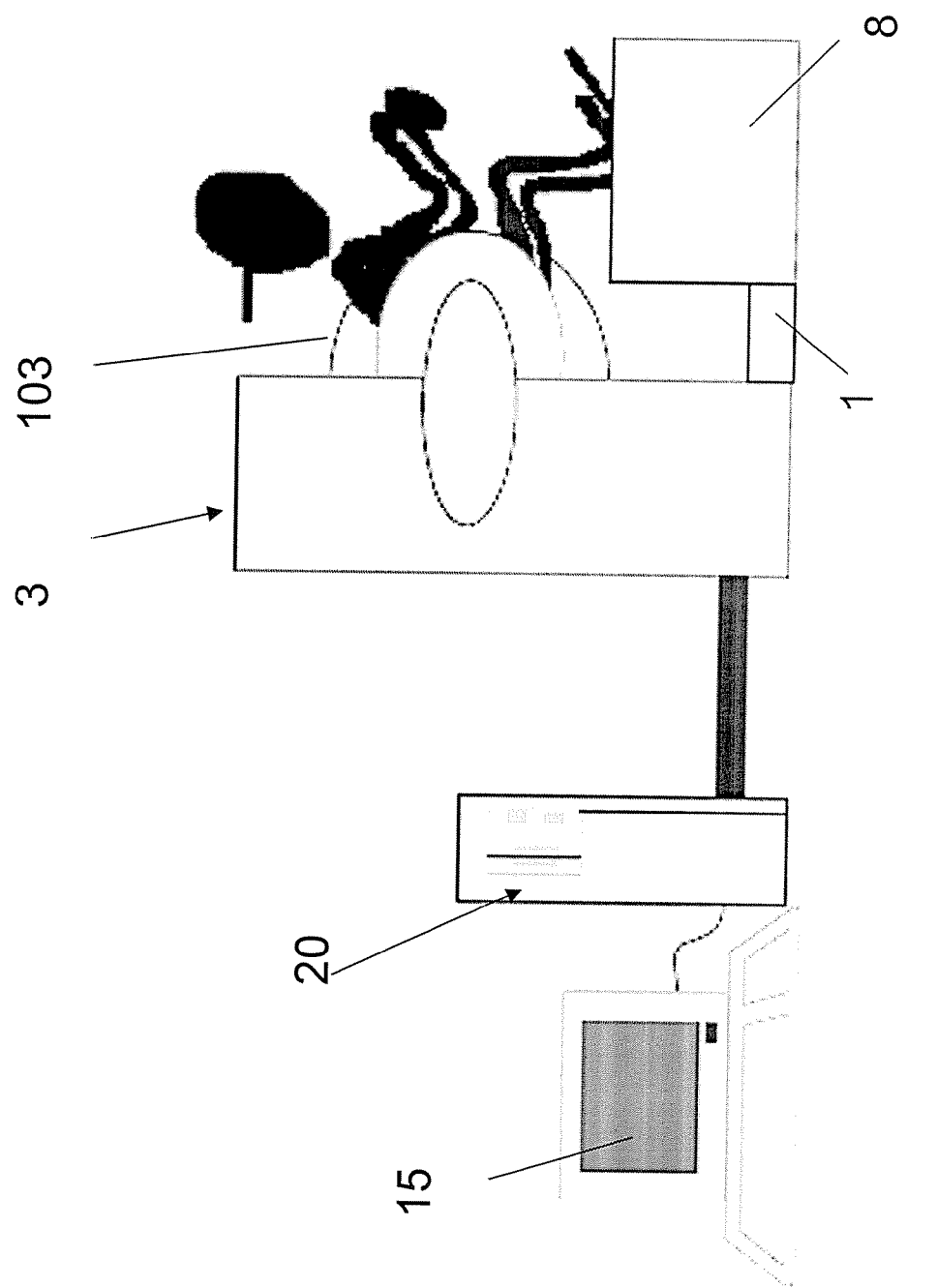
FIG. 6 is an embodiment of the device according to the present invention.
Figure 7:
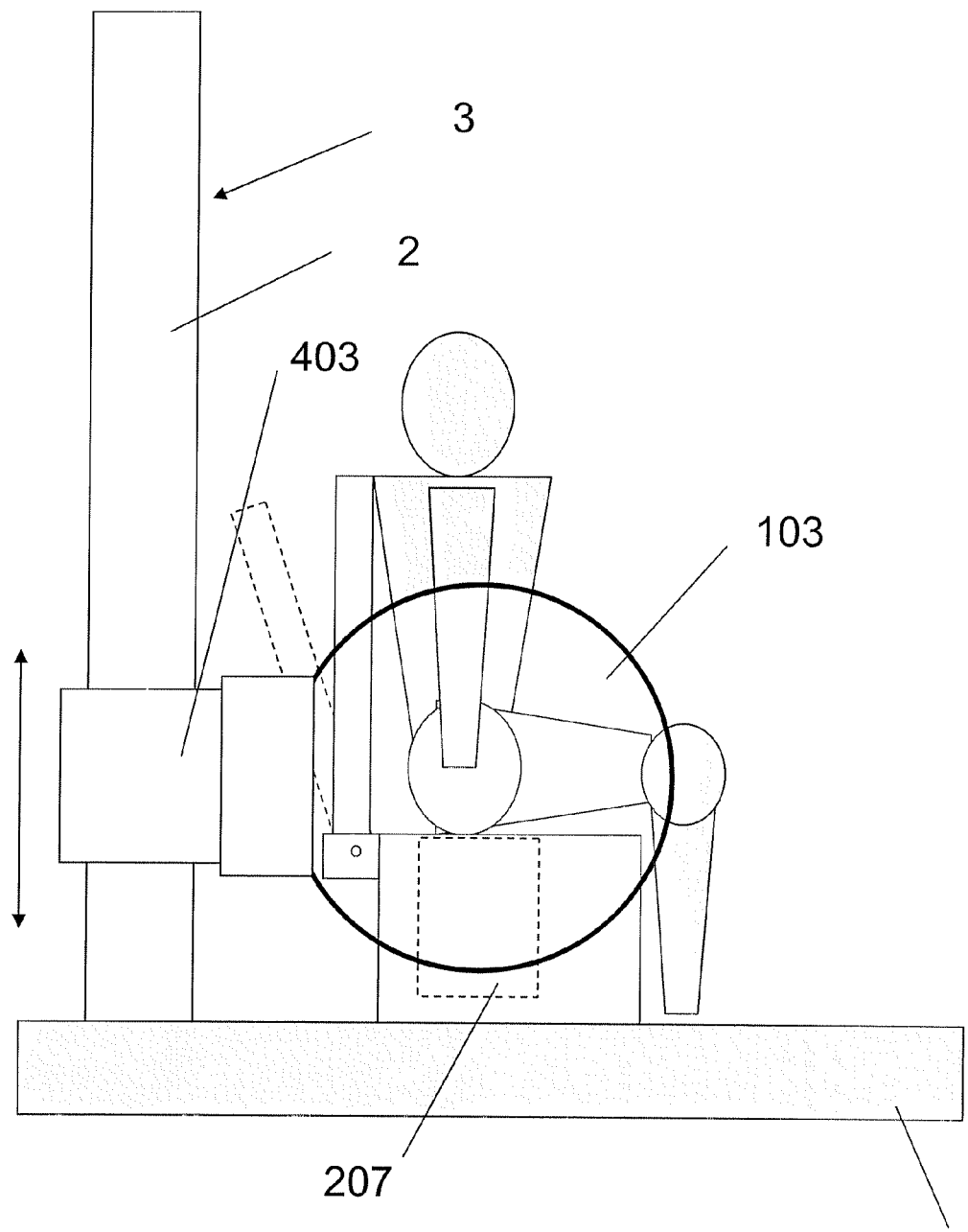
FIG. 7 is a diagrammatic side view of the MRI apparatus according to an embodiment of the present invention for the patient in the seated position.
Figure 8:
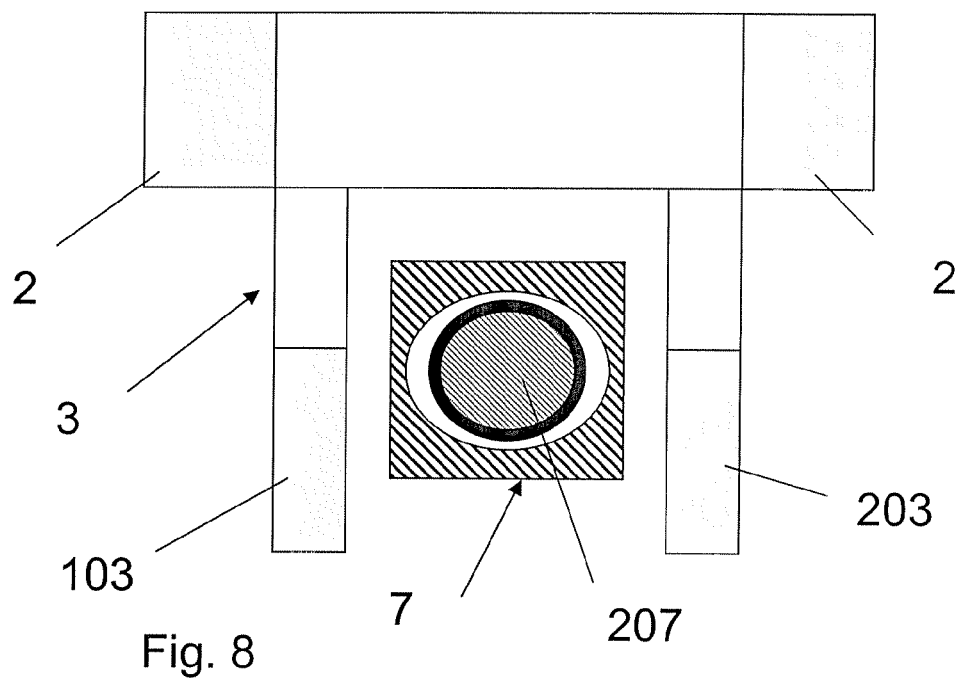
FIG. 8 is a diagrammatic top view of the MRI apparatus according to an embodiment of the present invention.
Figure 9:
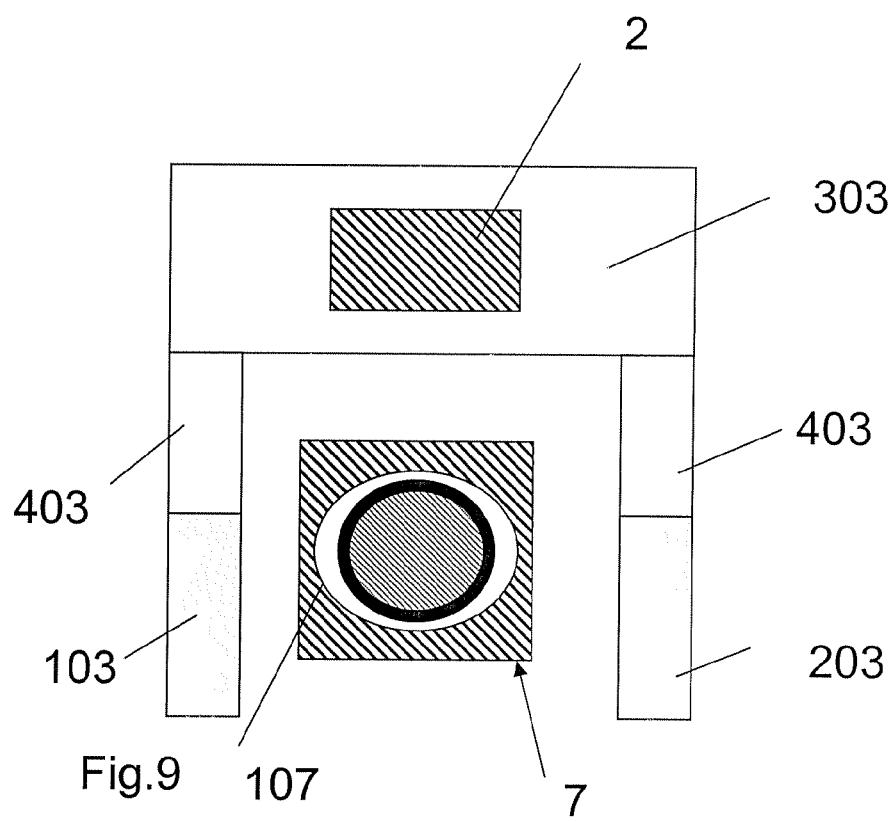
FIG. 9 is a diagrammatic top view of the MRI apparatus according to a further embodiment of the present invention.
Figure 10:
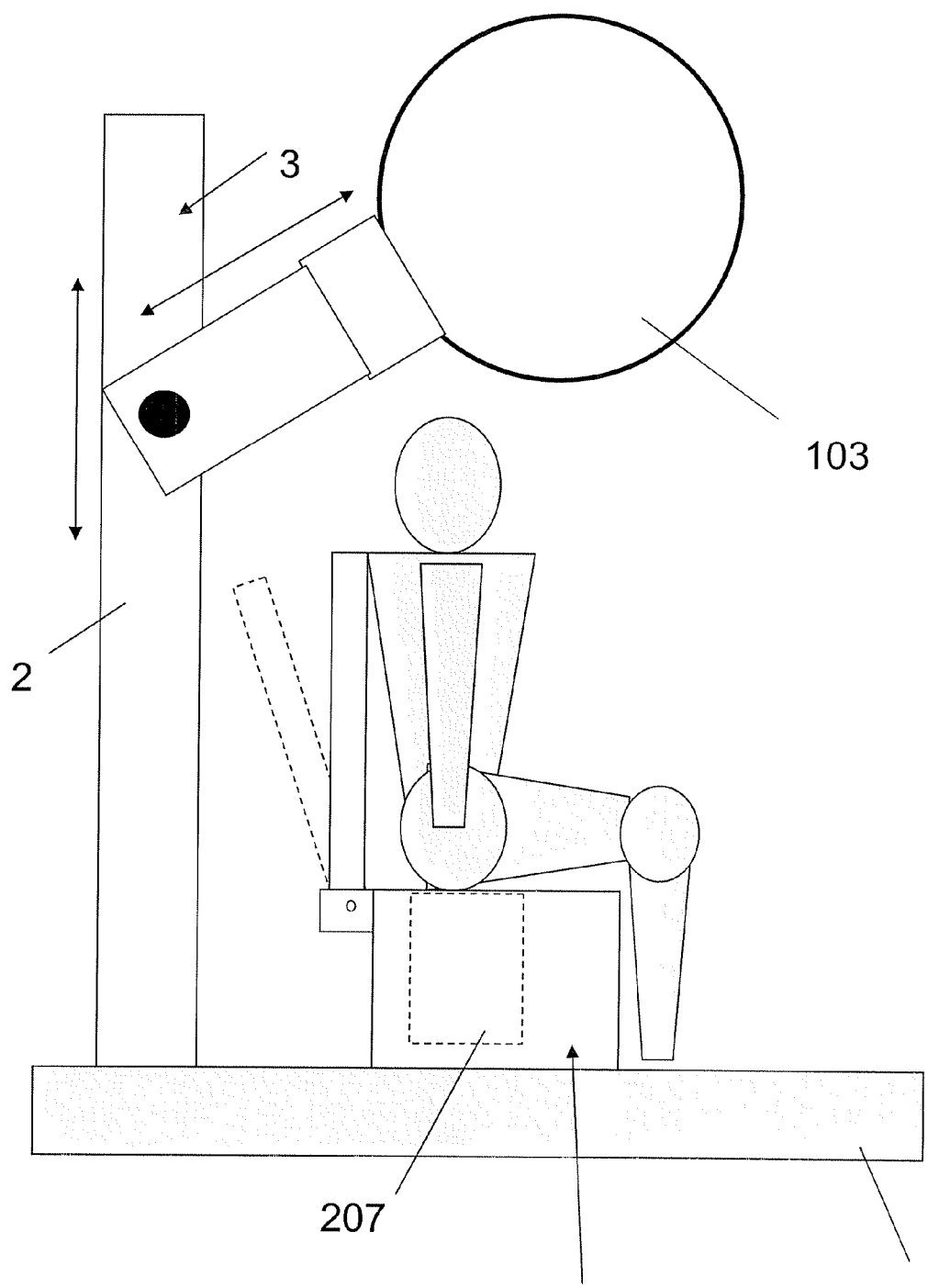
FIG. 10 is a diagrammatic side view of the MRI apparatus according to an embodiment of the present invention with the patient in the seated position.
Figure 11:
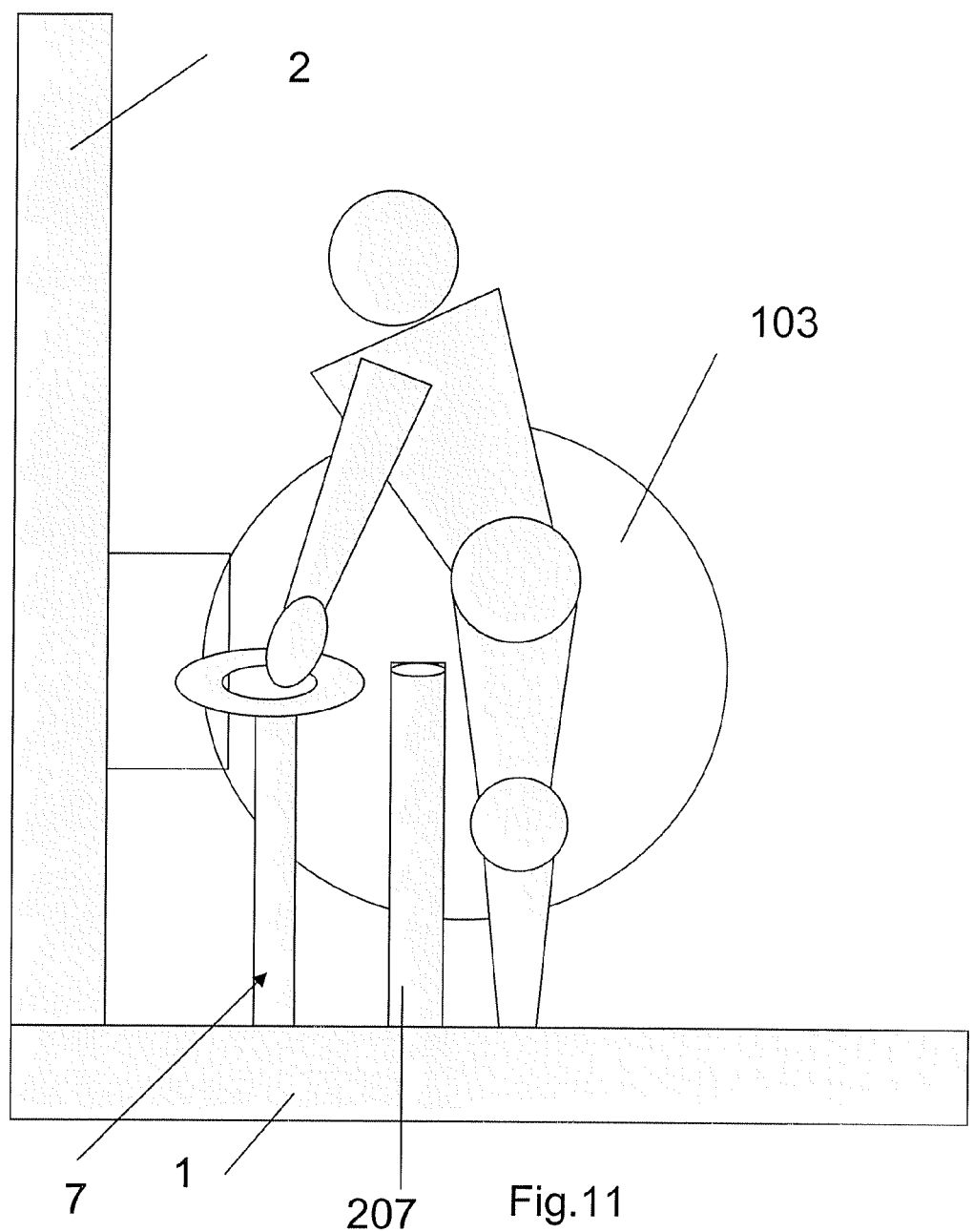
FIG. 11 is a diagrammatic side view of the MRI apparatus according to an embodiment of the present invention for the patient in the upright position

With reference to figures, particularly to FIG. 6, a diagnostic device for the anatomical region of the pelvic floor comprises at least an apparatus for acquiring images of the anatomical region of the pelvic floor by nuclear magnetic resonance, wherein there are integrated units for generating the film in CINE MR mode and a unit processing acquired images that provides to taken information from images about the state or conditions of objects reproduced in said images that support the morphofunctional evaluation by medical personnel in order to correctly make the diagnosis, to define the prognosis in a more precise way and for precisely monitoring the rehabilitative treatment.

Figure 1:
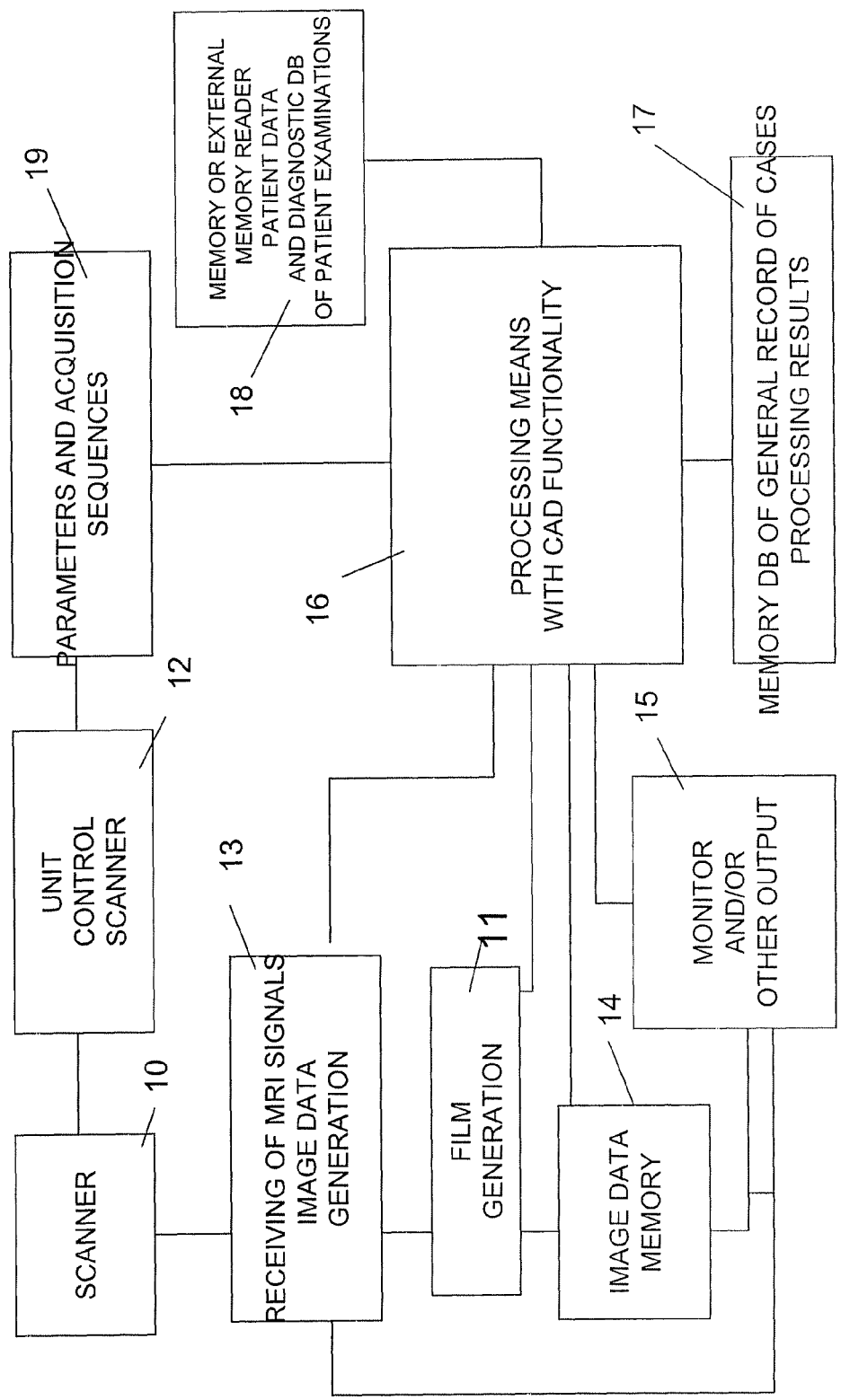
FIG. 1 is a block diagram of a device for acquiring and displaying MRI images according to of the present invention.
Figure 2:
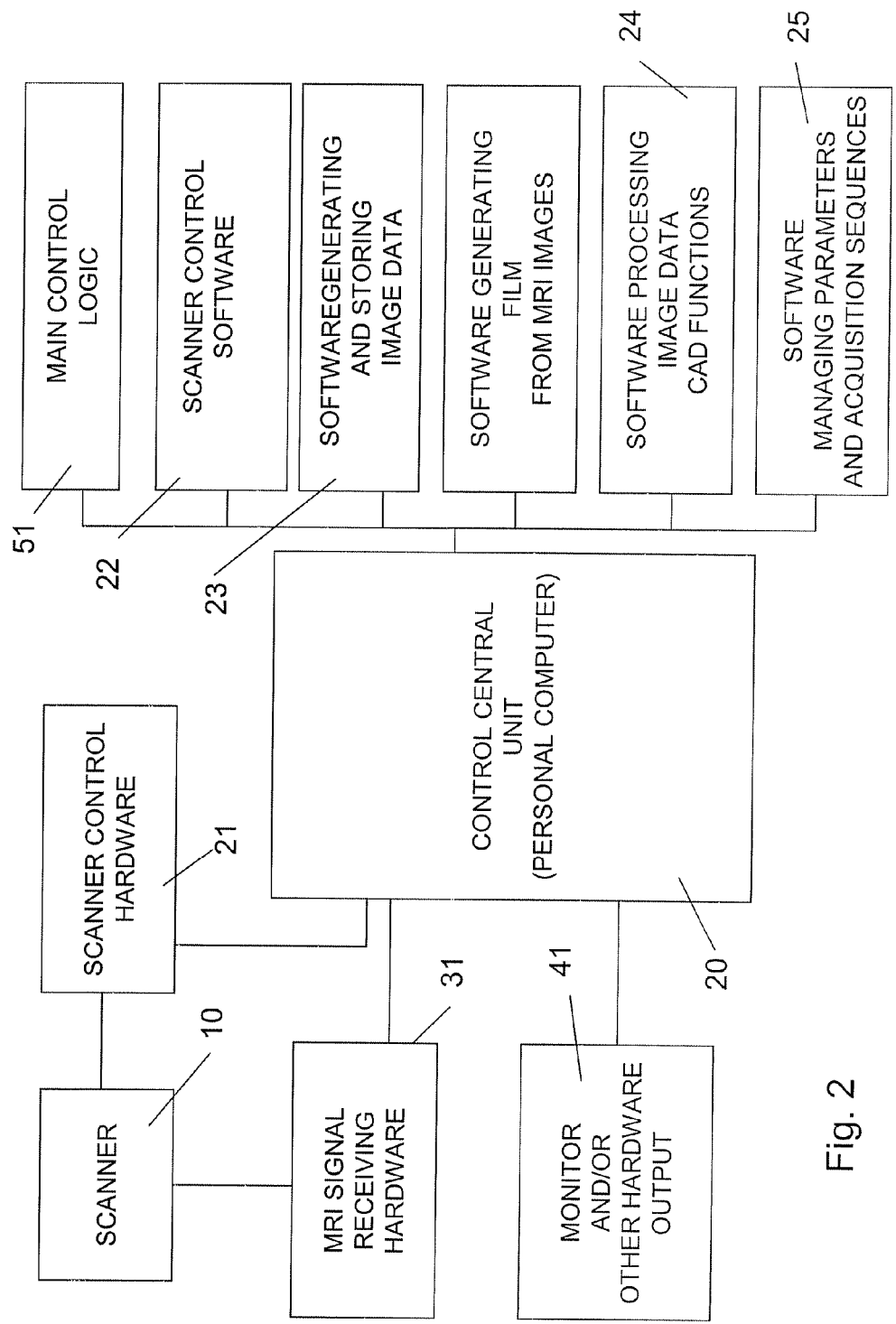
FIG. 2 is an embodiment of the present invention wherein means for acquiring MRI images, means for processing images, means for processing the film of the cinematographic type are composed of a combination of software and hardware and particularly of applicative programs that are executed by a main computer in common to acquiring means, to means for generating the film and to processing means.

FIGS. 1 and 2 show a block diagram of a device for acquiring and displaying MRI images. The device comprises a nuclear resonance magnetic imaging unit, a unit for generating the film of the cinematographic type by using one or more images of the MRI sequence as individual frames, and/or a unit having CAD functionality processing images for determining or measuring dimensions and/or morphologic parameters and/or values of dynamic deformation parameters of tissues and/or organs and/or structures or part thereof present in the body region under examination, particularly of the bladder and/or sphincter.

In FIG. 1 the scanner is indicated by 10 that is the unit for acquiring MRI images comprising the magnetic structure, gradient coils, receiving coil and the transmitting one, and further possible devices or means for acquiring resonance signals. Means for controlling the scanner and means receiving signals and generating image data are indicated by 12 and 13 and both are generally composed of electronic devices. Such means 12 and 13 can be also composed of combinations of software and hardware means and of software means loaded in a general hardware intended to execute the software, such as a main computer or also a personal computer as it will be shown below.

Image data generated by the unit 13 are stored in a memory 14 and therefore anytime they can be called up in order to be displayed by means of the monitor 15 or other output means or they can be immediately displayed apart from the storing.

The generation of the film and/or the processing of the image sequence occurs in real time i.e. during or immediately after said images have been acquired by means 11 such as programs processing images and/or processing data that can be loaded in memories of a computer and executed by it, for example a computer of the personal computer type or the like.

The data image processing unit having CAD functionality comprises processing means having CAD functionality that are indicated by 16 and to which there are provided or which call up image data of one or more images of the CINE MR film to be subjected to processing processes from memory 14, or from the unit receiving and generating image data 13 and/or possibly even from the monitor or from further possible output means 15 when they allow it.

The processing results can be in the form of alphanumeric data and/or as an alternative or in combination they can be in the form of static images and/or as an alternative or in combination they can be in the form of dynamic images i.e. image sequences such as films or the like.

Image processing means have different functionalities and are intended to define or to draw out from image data specific characteristics of images and/or of objects reproduced in the image. These means are composed of algorithms processing images, that is image data.

Each image and/or each image sequence is analyzed by analyzing image data relevant to a patient whose condition is not known by means of a predictive and/or classification algorithm, which predictive algorithm has been subjected to training and testing (learning) by means of data of a database of known clinical cases.

Results in the alphanumeric form and/or in the image or images form can be displayed on the monitor 15 or printed or personnel can have the access thereto by other means. Moreover in combination or as an alternative results are stored in a memory 17 with a general record of cases having both the task of having data of various examinations for each patient in order to allow the definition of treatment effects on the patient with the time goes by and the task of enlarging a database of known record of cases necessary for training and testing experienced algorithms that are used by CAD processing means 16 and that improve their performances with the time goes by and by the use thanks to a constant learning. As an alternative or in combination it is possible to provide also a reading/writing unit 18 of an external portable memory, such as a tape, a floppy disk, writable or rewritable CD or DVD or a so called smart card wherein data of each examination of each patient are stored together with other data obtained by other examinations.

At least a part of processes for acquiring, generating and displaying images carried out by the MRI imagining apparatus are composed of software programs that are executed by computers that are in said MRI imaging apparatus, in said computer there being loaded or can be loaded and executed programs for processing images and/or data, included programs for generating the film CINE MR, that are means for processing images and/or image data.

Referring to FIG. 1 there is provided a unit generating and/or setting parameters and image acquiring sequences by nuclear magnetic resonance that is indicated by 19, receiving input setting command signals or command signals changing the setting on the basis of which it generates parameters for setting the scanner 10 and/or it determines image acquiring sequences and it provides said parameters and said sequences to the unit 12 controlling the scanner for acquiring images. Said unit is composed of a combination of hardware and software indicated in the diagram of FIG. 2 by 25. Particularly said software can allow to manage and change the number of images to be acquired in the selected time interval in order to set, depending on decisions of the medical operator, the acquisition of high contrast and/or resolution static images for analysing anatomical details under interest or the acquisition of fast images able to allow the generation of a film wherein individual frames are acquired during at least a part of the natural and/or induced evacuation or micturition physiologic process. Said film helps in evaluating the functionality and/or dysfunctionality degree of organs during the dynamic phase. The device comprises also software for comparing the two types of image, the "fast" one and the "slow" one in order to help in evaluating the follow up of the treatment to which patients are subjected. Particularly shapes and/or dimensions and/or values of dynamic deformation parameters determined from acquired images of the body under examination along a time interval coinciding or comprising at least a part of the length of the physiologic process evacuating solids and/or liquids are compared and/or blended with shapes and/or dimensions and/or values of static deformation parameters determined by means of a process acquiring MRI images and processes carrying out the segmentation and/or rendering of reproduced objects and particularly tissues and/or organs and/or structures or parts thereof present in the area of the body under examination in a time interval that does not comprise the evacuation physiologic process.

With reference to FIGS. 2 and 6 the device provides a central controlling unit 20 that for example is composed of a personal computer or two or more personal computers working in parallel one with the other for executing various programs each one of which is intended to execute specific tasks when such task is expressly required by a command of personnel or by a processing procedure automatically carried out and controlled by a control logic represented by the memory area 51.

The memory area 22 represents the program controlling the MRI scanner, considering that the term scanner means various operating units, main or secondary ones such as the magnetic structure, gradient coils and the transmitting coil and operating units necessary to detect and receive magnetic resonance signals.

Operating units in the scanner are controlled by hardware controlling units indicated by 21 and whose operation is controlled by a program controlling the scanner indicated by 22. Output resonance signals from the scanner are processed by a unit receiving MRI signals generating image data from MRI signals and that comprises hardware means indicated by 31 and are controlled by a program generating and managing image data such as particularly the storage indicated by 23. Means for processing images and/or image data and means for generating the film by using individual acquired MRI images, are composed of one or more program modules that are executed by the same central controlling unit 20.

Medical personnel can access the results by one or more monitors 41 controlled by the central unit 20 and by specific command programs.

Figure 3:
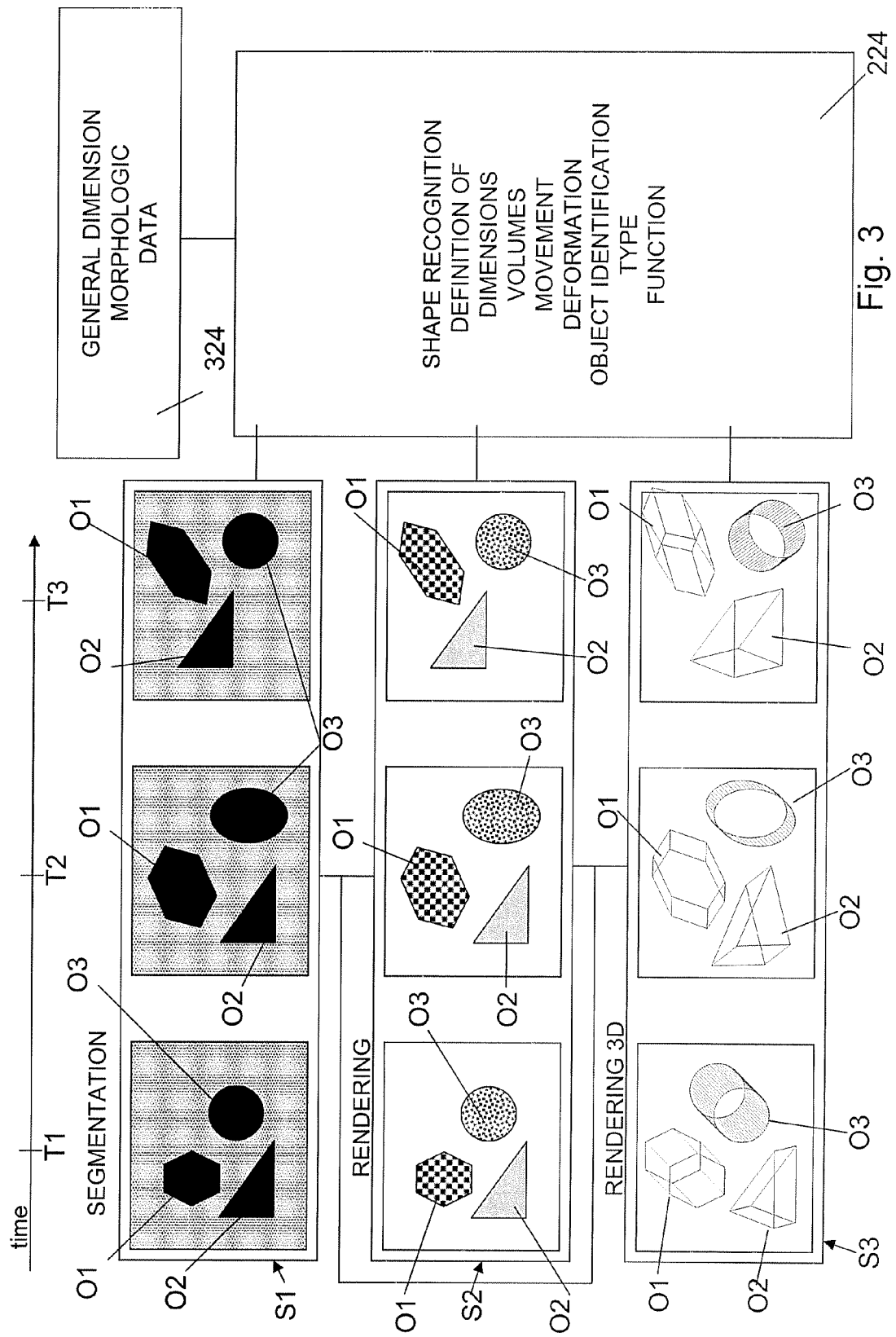
FIG. 3 is a block diagram of an example of the segmentation and rendering process, wherein the conventional image segmentation and rendering process is integrated with typical morphologic and/or dynamic functional data for real objects reproduced in images.
Figure 4:
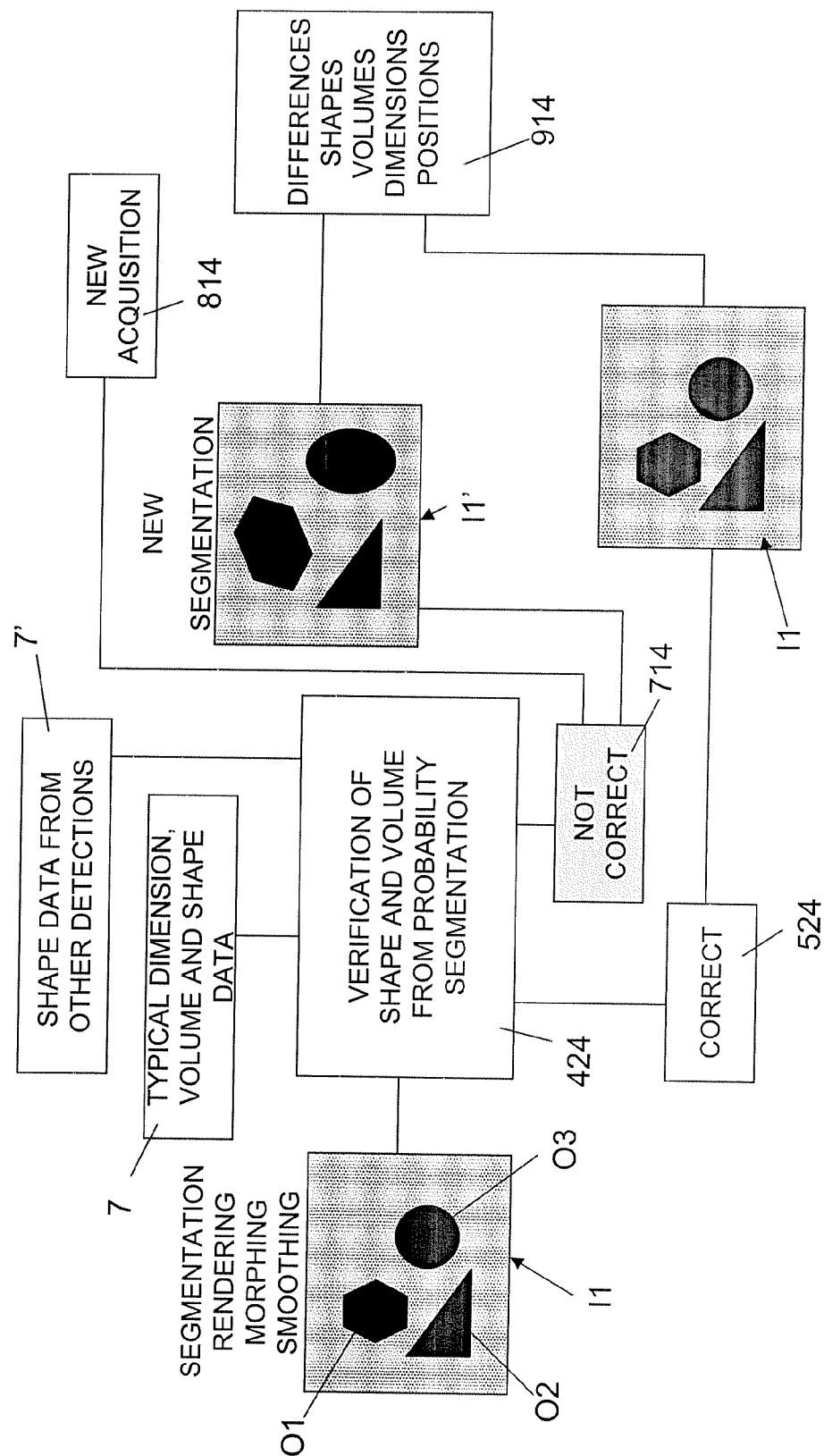
FIG. 4 is a block diagram of means for processing images specifically provided in an embodiment of the present invention for the diagnostic help of the pelvic floor anatomical region.
Figure 5:
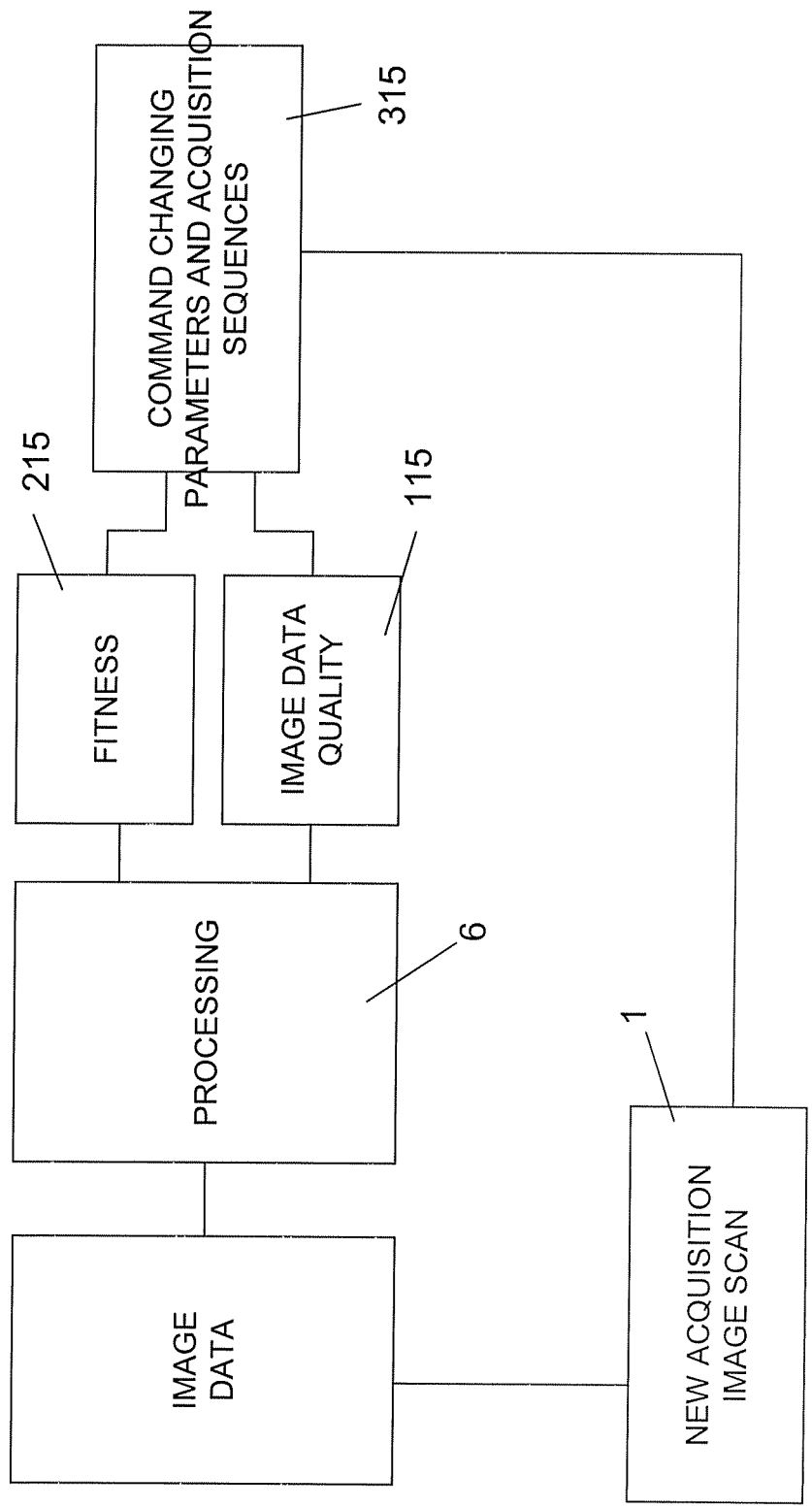
FIG. 5 is a block diagram of an embodiment of the present invention with regards to an example of automatic or semi-automatic means for the interaction between means acquiring images and means processing images for particularly optimally setting acquiring means with reference to processing means.

FIGS. 3 to 5 schematically show an example of different processes for treating resonance signals and/or image data. With reference to FIG. 3 images of the sequence or images composing the film in the cineRM mode are subjected to segmentation for identifying subsets of pixels or voxels in images corresponding to the representation of an object or a structure provided in the three-dimensional area of which the image has been acquired and/or intersected by the scanning plane. Once said subsets are defined the processing process provides the identification of the real object corresponding to each subset of pixels or voxels as regards the type of tissue or organ, and the generation of virtual objects each one corresponding to said real objects and each one composed of the subset of pixels or voxels determined by means of the segmentation.

In each image or image sequence it is possible to recognize the object and to determine the behaviour in time of each object as regards the position, orientation, shape, dimensions and volumes. Particularly said processing allows to determine the volume of the bladder under the full, empty and/or partially empty condition and/or the volume of the sphincter under various functional conditions, said dimensions and/or morphologic parameters being used as parameters for the comparison with corresponding dimensions and/or morphologic parameters of the same organs obtained from a database of known clinical cases.

In FIG. 3 S1 indicates a sequence of images acquired in different subsequent time moments indicated by T1, T2, T3.

In this case they are images of the same anatomical region acquired along the same scanning plane for 2D images or within the same scanning volume for 3D images. The sequence of MRI images is acquired along one or more predetermined section planes or inside a predetermined three-dimensional area, which planes intersect and/or which three-dimensional area contains at least a part of the pelvic floor. In order to allow the examination of the pelvic floor during the dynamic evacuation phase, the sequence is acquired along a time interval coinciding or comprising at least a part of the length of the physiologic process evacuating natural solids and/or liquids carried out on the basis both of a natural stimulation and an induced stimulation or during the simulation of physiologic processes evacuating solids or liquids by introducing foreign bodies or substances simulating natural products.

As it is schematically shown there are provided three objects 01, 02, 03 in the region that move and/or get deformed with the time goes by and representing in images three different objects provided in the volume of the body under examination subjected to the image acquisition. These real objects for example can be three different types of tissue and/or three different types of organs or the like.

Once objects and the behaviour in time thereof such as defined above are determined it is possible to generate a virtual image a kind of virtual copy of the real world wherein objects and behaviour are further highlighted by rendering, morphing, smoothing processes and other methods generating virtual realities.

Sequences S2 and S3 schematically show an example of 2D and 3D rendering of the behaviour of objects recognized in the sequence S1 by means of the segmentation.

In FIG. 3 processes for recognizing shapes, determining dimensions and volumes, for moving, orienting and changing the shape, as well as the identification of real objects reproduced by virtual objects with reference to the type and the function of these real objects is indicated by a subset 224, while the latter is interfaced with a further subset 324 providing morphologic and dimension data typical of real objects that can be compared with the ones determined by images.

Rendering and segmentation allow to display structures in their three-dimensional form but also to provide evaluations about their functionality and about their involvement degree in organ prolapse.

FIG. 4 shows a further system for verifying the segmentation and generation of renderized images. There is provided a step for verifying and correcting results of the segmentation and/or rendering process wherein shapes and/or dimensions and/or values of dynamic deformation parameters determined by acquired images of the body under examination are compared with shapes and/or dimensions and/or values of dynamic deformation parameters determined by identical processes acquiring MRI images and processing segmentation and/or rendering for a certain number of known clinical cases or determined on the basis of average typical values or typical value ranges provided for said shapes and/or dimensions and/or values of dynamic deformation parameters of reproduced objects and in particular of tissues and/or organs and/or structures or part thereof that are present in the region of the body under examination.

A maximum differentiation threshold is established as regards increase and/or decrease of shapes and/or dimensions and/or values of dynamic deformation parameters determined by acquired images of the body under examination from the corresponding ones relevant to known clinical cases and/or the ones typical for organs and/or tissues and/or structures or part thereof present in the region of the body under examination.

When the maximum differentiation threshold is overcome, at least an error warning and a request for manually repeating the segmentation and/or rendering and/or morphing and/or smoothing and/or MRI image acquisition process is generated. As an alternative the segmentation and/or rendering and/or morphing and/or smoothing process is automatically repeated and/or a new MRI image acquisition is carried out.

It is possible to provide for the verification process and/or the step repeating the segmentation and/or rendering and/or morphing and/or smoothing and/or MRI image acquisition process to be iteratively repeated for a predetermined number of times and/or till the comparison provides difference values that are below the maximum differentiation threshold.

In this case in FIG. 4 the image segmented and possibly further subjected to reconstruction by means of rendering possibly in combination with treatments of the morphing or smoothing type, is analysed with reference to the shape, volumes and dimensions of objects 01, 02, 03 identified in said image I1 and possibly also to topologic and dimension relationships of said objects into a verification unit 424. To this unit 424 there are provided morphological and/or volume and/or dimension data typical of objects that are considered corresponding to the ones reproduced in the image I1 and indicated by 01, 02, 03. Such data can be relevant to an average value and/or a range comprised between minimum and maximum values. Moreover typical data can also consider not standard values corresponding to typical pathological conditions. Processing means can comprise such data in the database of clinical cases stored for example in the memory or memory area 17 such as indicated in FIG. 1.

Moreover it is possible to carry out the comparison with other morphologic, topologic and dimension data obtained by other measuring or analysing methods, such as by other means for acquiring images different from the magnetic resonance such as ultrasound, radiologic means etc. said data being included in the database of clinical cases too and stored in a dedicated memory area that in FIG. 4 is indicated by 7'.

Particularly it is possible to provide the generation of a database of examinations of each patient and the comparison of results of previous examinations with results of following examinations, in order to determine the evolution of the disease particularly with reference to therapy effects.

When the result of the verification system shows that morphologic and/or dimension and/or topologic and/or deformation data of objects derived from corresponding virtual objects are consistent with corresponding typical data it is possible to go on as indicated by the box 524 and by the image I1 and in this case it is possible for example to determine differences in shape, dimension, deformation and position of real objects determined by corresponding virtual objects with respect to corresponding shape, dimension and position data of real objects such as provided in the database of clinical cases 7 and 7' as indicated by the functional box 924. Moreover these differences can be used as a measure for defining the existence of a pathologic condition and/or for evaluating the evolution of the disease if it is present.

The dynamic functional analysis of all diseases of the pelvic floor under conditions that can be superimposed to the evacuation physiologic process provides that a differentiation threshold value is determined for the discrimination of the condition of presence or absence of a disease and/or a scale of different threshold values for determining the evolution of the disease, based on values for said shapes and/or dimensions and/or values of dynamic deformation parameters of reproduced objects and particularly of tissues and/or organs and/or structures or part thereof present in the region of the body under examination determined by known clinical cases.

Values for said shapes and/or dimensions and/or values of dynamic deformation parameters of reproduced objects and particularly of tissues and/or organs and/or structures or part thereof present in the region of the body under examination and determined by the image sequences of patients under examination, are compared with said threshold value discriminating the presence/absence of the disease and/or with said scale determining the evolution of the disease. The comparison determines for the specific patient the indication of the probable presence/absence of the disease and/or the probable evolution of the disease.

A further embodiment provides that, in order to evaluate the presence or absence of a disease and its development degree, for each image or image sequence a parameter measuring the average intensity or brightness is determined for the whole image and/or for one or more limited regions thereof that is compared with an identical reference parameter. By defining a threshold discriminating the presence/absence of the disease and/or a scale of values determining the evolution of the disease, and by comparing made measures with said threshold a measure of the presence/absence of the disease or of the evolution degree thereof is obtained. Particularly the reference parameter and/or the discrimination threshold and/or the scale measuring the evolution of the disease are determined by processing data and particularly image sequences of clinical cases being part of a database of known clinical data.

Parameters relevant to the presence/absence of the disease and to the evolution degree of the disease obtained by the segmentation and/or rendering process and by the comparison with corresponding data of the clinical database and parameters relevant to the presence/absence of the disease and/or the evolution degree thereof obtained by the analysis of average intensity values of image pixels or voxels and/or parameters relevant to the presence/absence of the disease and/or the evolution degree thereof obtained by means of the analysis pixel by pixel or voxel by voxel with the help of predictive and/or classification algorithms and/or parameters relevant to the presence/absence of the disease and/or the evolution degree thereof obtained by one or more further analysis and processing processes are input variables of a final classification algorithm or of a predictive algorithm that has been subjected to training and testing on the base of a database of known clinical data and providing the final and recapitulatory indication about the probable presence/absence of diseases and/or the probable evolution condition thereof.

Such as shown in FIG. 4 when the verification unit 424 establishes that there is no compatibility between morphology and/or dimension and/or position of real objects determined by virtual objects with respect to shape, dimensions and positions of real objects obtained by the database of clinical cases, so image data I1, that are segmented, and/or further renderized and/or subjected also possibly to morphing and/or smoothing are considered as wrong 614 and it is possible to repeat the segmentation and/or rendering and/or possibly morphing and/or smoothing process such as indicated by the image I1' or also to provide a new image acquisition of the body under examination such as indicated by 924.

It is to be noted however that all functional boxes 424, 824, 924 are composed of program modules that are executed or can be executed upon the calling up from the central processing unit and resident in a memory thereof or can be loaded in said memory.

FIG. 5 shows a block diagram of an interaction subsystem between the apparatus for acquiring images and means processing them.

Image data of the receiving unit 13 are provided to the processing unit 16. CAD processing means obtain information from image data by using algorithms of the statistic, predictive, or evolutive type that however together with output data provide also reliability or error parameters of output data. Moreover resonance signals from which image data are taken can be analysed with regards to their quality with reference to some quantities that are important for the image quality and particularly, but not limited thereto, are signal/noise ratio, resolution, contrast.

Therefore interaction means can have one or more different sections for determining parameters and acquisition sequences one of these acting on the basis of reliability parameters of the output of CAD processing means and the other one acting on the basis of quality parameters of resonance signals and/or image data such as indicated by 125 and 225. Therefore the two sections provide information relevant to the quality of image data with reference both to mere acquisition steps and to reliability of output data of processing means, so in the quality verification section 325 by means of a comparison between threshold values for relevant reliability parameters and/or for quality parameters of resonance signals and/or of image data indications are determined about the fact if it is necessary to provide to determine new setting parameter values and/or to change acquisition sequences of images and so to send a command to the unit generating acquisition parameters and/or sequences rappresented by the optimization software. On the basis of the command of the verification section the optimization software i.e. the generating section provides to generate modified setting parameters and/or to change the sequence or sequences in use.

Such new values of setting parameters and/or changes of acquisition sequences of images are therefore provided to the scanner 10 for carrying out a new scan for acquiring images.

Image data obtained by the new scan can be subjected again to steps described above for verifying if changes of settings have lead to desired improvement results with regards to quality of resonance signals and/or of image data and in combination or as an alternative with regards to the reliability of outputs of processing means.

Steps indicated above can be also interactively repeated till a certain amount of interaction steps is carried out and/or till the quality of resonance signals and/or image data and/or the reliability of outputs of processing means does not reach or overcome predetermined minimum threshold values.

From the above it is clear that the method allows to measure morpho-functional parameters intended to highlight the presence and the degree of a disease involving the pelvis area and to allow the follow-up during the therapy. Particularly this method can be applied by means processing images and/or generating films cine RM starting from acquired MRI images, integrated by a MRI apparatus dedicated to the acquisition of images of the pelvic floor.

Referring to FIGS. 6 to 15, a not limitative example of an apparatus for acquiring images of anatomical region of the pelvic floor by nuclear magnetic resonance, according to the present invention, first comprises a base 1 and a supporting element 2 in the form of a vertical wall or column. A magnetic structure 3 is secured to said supporting element 2 such to project therefrom. The magnetic structure 3 comprises two opposite poles 103 and 203 that are oriented paralelly to the vertical supporting wall or column 2.

Said poles 103 and 203, with a diameter lower than the average height of a human being, are spaced apart at a predetermined extent and are connected one with the other by a wall or connection element 303 extending parallely to the vertical supporting column or wall 2 and that is secured to said wall 2 by means of the combination of a longitudinal rack 4 that is perpendicular to the element or transverse wall 303 connecting poles 103, 203 and at least a pinion provided on the wall 303 connecting poles 103, 203 or vice versa.

The rack 4 provided in a housing in the supporting wall 2, or directly on the surface of the supporting wall or column 2, is parallel to poles 103, 203 and perpendicular to the magnetic field generated therefrom.

The combination of at least a rack 4 and at least a motor-driven pinion guarantee the motorized movement in the vertical direction of the magnetic structure 3 on the rack 4 with respect to the supporting wall 2.

As an alternative and/or in combination the magnetic structure 3 is slidably supported on the supporting wall or column 2, in the direction perpendicular to the magnetic field generated between the two poles 103, 203, by means of a combination of guides and slides, there being provided motor-driven elements in order to obtain the correct positioning of the magnetic structure 3 with respect to the anatomical region to be analysed. However, motor-driven means can be partly absent, and movements can be manually carried out at least partly. Above all in this case it is possible to provide automatic sliding limiting devices and/or mechanical means stopping the sliding in one or both vertical directions. Said limiting devices can be composed for example by a plurality of hydraulic cylinders provided at predetermined positions within sliding means, which cylinders with a command can be brought from an idle, retracted position or flush with the plane of sliding means such as guides and slides, to an abutment active position taken outwardly and having the function of sliding limit stop. Said limiting devices can be also provided in the case of a motor-driven movement having the safety function.

Means used to obtain the movement are not necessarily of the electrical type and can be of pneumatic, hydraulic type or the like.

Further embodiments can provide the connection element 303 to have a hole at a position corresponding to half the distance between the two poles 103, 203 and the supporting element 2 to be like a column engageable in said hole such to allow the magnetic structure 3 to vertically slide. As an alternative the MRI apparatus comprises two supporting elements 2 like columns put one near the other at a predetermined distance and between which the magnetic structure 3 comprising the two poles 103, 203 and the connection element 3 is associated in a sliding way.

A further embodiment provides that the magnetic structure 3, particularly opposite poles 103 and 203 each one are borne by a supporting means 403 associated to the supporting column or wall in order to have the possibility to translate and/or rotate and/or slide with respect thereto.

Particularly means 403 supporting magnetic poles 103, 203 are pivoted on the supporting wall 2, particularly on vertical sides of said wall that are parallel to planes upon which poles 103, 203 rest in order to allow poles to pivot at 180° such that their position is adjustable with respect to the part of the body under examination, particularly with respect to the height of the pelvis region. As an alternative means 403 supporting poles 103, 203 can slide upwardly or downwardly with respect to the vertical supporting wall or column 2 by a combination of rack/pinion and/or guides/slides positioned on the element 403 supporting the magnetic poles 103, 203 and on the supporting wall 2 respectively, particularly on vertical sides of said wall 2 that as a consequence will have such a width to allow to have a detecting cavity between poles 103, 203 sufficient for housing the part of the body under examination.

In combination with means for adjusting the height of magnetic poles 103, 203 with respect to the patient as described above, it is possible to provide supporting means 403, and consequently poles 103, 203 to be secured to the supporting wall or column 2 such that can be move near or away from the supporting wall 2.

The magnetic structure 3 delimits a cavity for housing at least a part of the body and/or at least a part of an organ and/or anatomical region under examination. Means for positioning the patient 7 are provided inside the cavity housing at least a part of the body and/or at least a part of an organ and/or of the anatomical region under examination, and have such a shape to make possible the simulation of the position taken by the patient during the physiological process evacuating solids and/or liquids in the seated position and/or in the upright position. Positioning means 7 are mounted on the base 1 of the apparatus and, according to a further characteristic, can slide according to a direction parallel to the two poles 103 and 203. That can be obtained in a way similar to what has been previously described as regards the movement of the magnetic structure 3.

The magnetic structure 3 is substantially of the dedicated type, i.e. it forms an imaging volume shorter than the average height of adult patients and so it is necessary to provide the possibility to move poles 103, 203 with respect to the part under examination and/or the part under examination with respect to poles 103, 203, in order to centre at least a part of the body under examination, particularly the anatomical region of the pelvis, inside the imaging volume wherein values of the magnetic field are such to guarantee the acquisition of MRI images.

The cavity delimited by the magnetic structure 3 has an open side allowing the patient to reach by himself or by the help of supports like wheelchairs, crutches or the like the area where images are acquired for the diagnosis.

Moreover the cavity has such a shape and dimension to allow the housing of at least a part of the body under examination, particularly the anatomical region of the pelvis in the seated position and/or upright position.

In order to make easier the process for acquiring images an embodiment provides positioning means 7 to be mounted as to rotate with respect to the base 1 by means of a combination of guides or slides, motor-driven means being provided for correctly arranging positioning means 7, and so the part of the body under examination, with respect to the magnetic structure 3. In one embodiment circular slides are provided below positioning means 7, that in this specific case can be a chair-like element, which slides are engaged as to slide in guides provided on the base 1 of the apparatus, or vice versa. As an alternative or in combination with the system of guides and slides it is possible to provide at least a rack and a pinion driven by a motor guaranteeing the circular motor-driven movement of the positioning element 7 in both directions.

In one embodiment it is possible to provide the magnetic structure 3 to rotate with respect to the patient, by manufacturing a semi-circular supporting frame or wall 2 allowing to move the magnetic structure about the part of the body to be examined by means of a combination of guides and slides and/or rack and pinion placed on the magnetic structure 3 and on the supporting frame and/or wall 2 respectively.

In a preferred embodiment said positioning means 7 are composed of at least a chair element intended for simulating the seated position taken during the physiological process evacuating solids and/or liquids.

Figure 12:
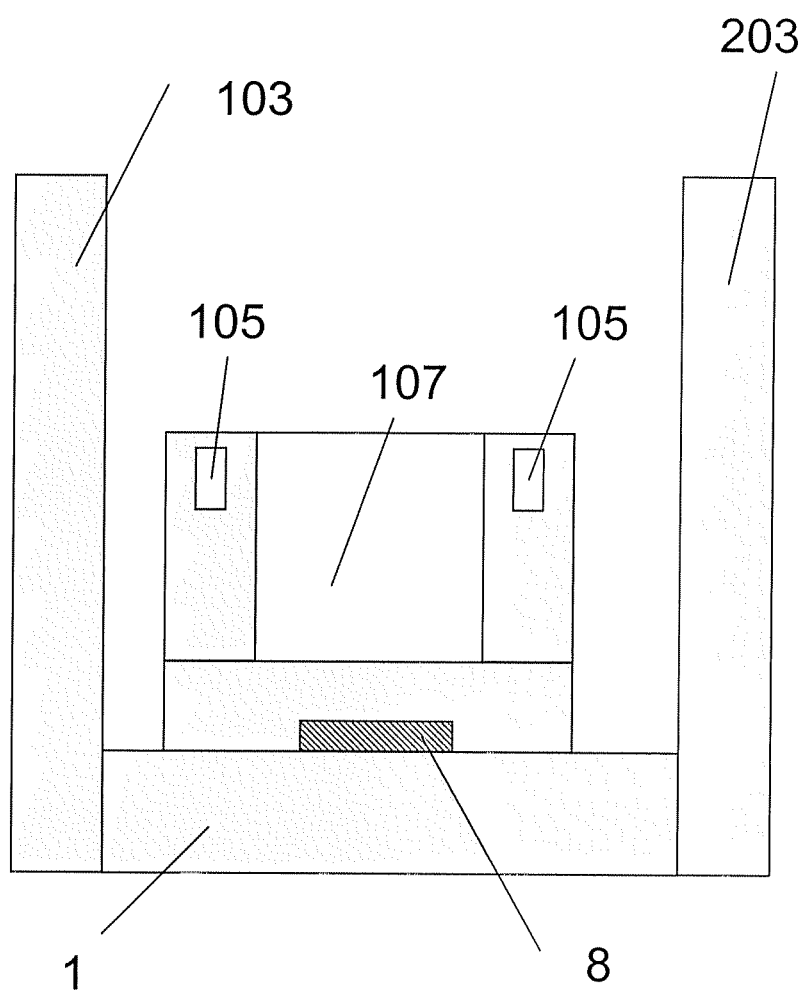
FIG. 12 is a diagrammatic front view of the MRI apparatus provided with a chair element like a toilet bowl.
Figure 13:
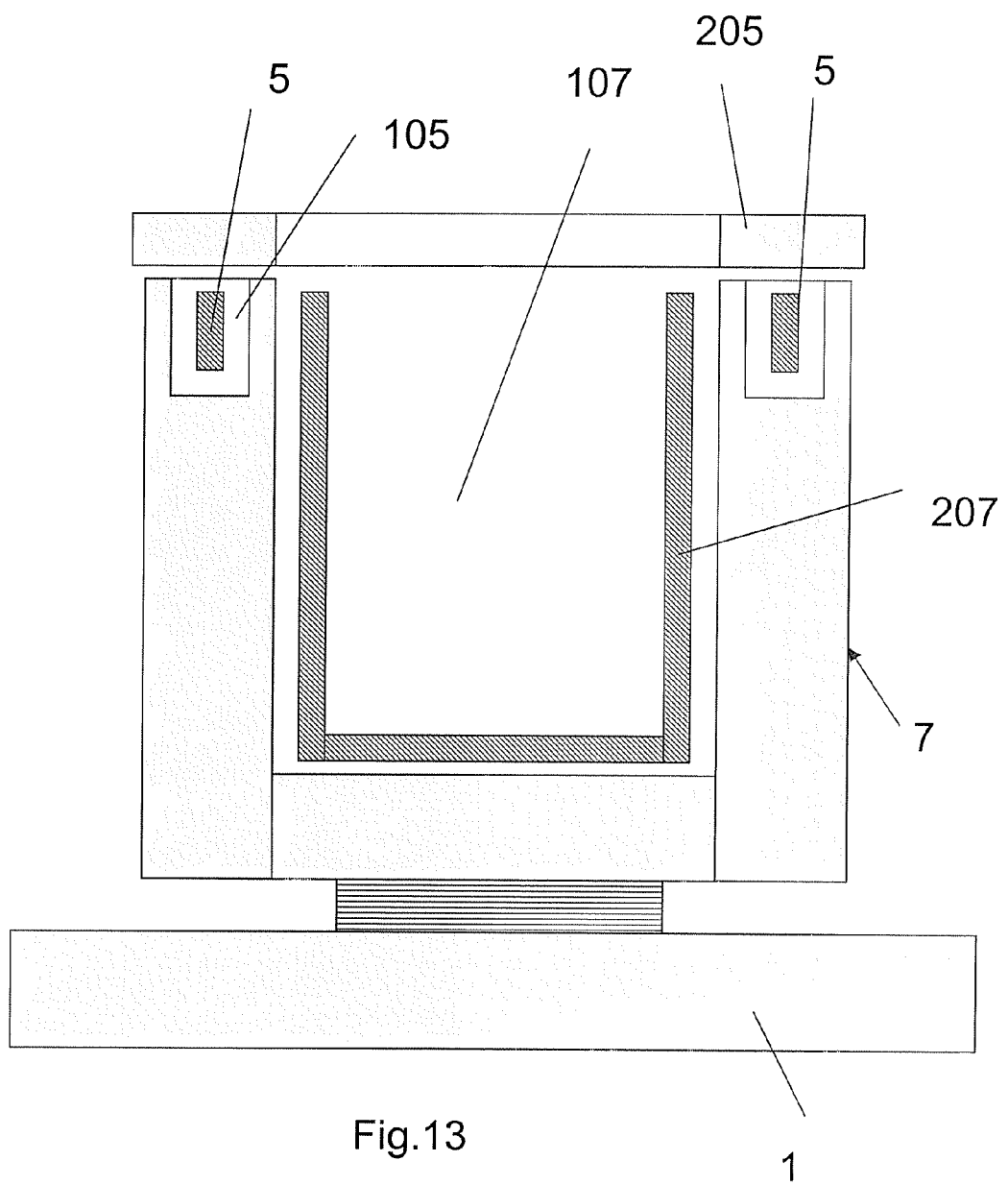
FIG. 13 is a chair element according to an embodiment of the present invention.

With reference to FIGS. 12 and 13, said chair element is like a toilet bowl made of an electromagnetically transparent material i.e. made of a not magnetic and/or not metallic material in order not to interfere with the process acquiring images, having an upper ergonomic sitting side for the patient in order to improve the comfort and with a central cavity 107 obtained in the thickness of the chair element for collecting liquids and/or solids produced or used during the diagnosis. Particularly inside the cavity 107 of the chair element there is provided a collecting element 207 for natural solids and/or liquids and/or foreign bodies or substances simulating natural products, composed of bags, soft or rigid containers, trays or the like such to guarantee cleanliness during the session acquiring images and after the treatment of each patient.

In order to improve cleanliness both for the patient and for personnel using the MRI apparatus inside the cavity housing the body under examination and above all at the pelvis level and on parts of the apparatus that even only casually can contact the body under examination or a part thereof or liquids and/or solids used and produced during the diagnosis, there are provided means for automatically cleaning and/or disinfecting said cavity and parts included therein, when the process for acquiring images ends.

In order to obtain MRI images necessary to make the diagnosis at least a coil 5 for receiving MRI signals is integrated in said chair element and/or in an axial extension thereof in the direction of the element collecting liquids and/or solids.

With reference to FIG. 13 in the chair element at a region substantially coinciding with or flush with the pelvis anatomical region of a patient under examination seated on said element there is provided at least an housing 105 for at least a means receiving MRI signals, particularly a receiving coil 5. In the shown embodiment the housing and the receiving coil 5 are at the pelvic floor of the patient, with reference to the seated position of the patient.

On the upper face of the chair element there is provided an element 205 closing the housing of the receiving coil 5 that can be removed or pivoted for taking out or housing the receiving coil 5. The element 205 closing at least one housing 105 of the receiving coil 5 can be removed for taking out or housing said receiving coil 5.

Said closing element 205 can be like a board for toilet bowls and said board can be pivotally raised or it can be composed of a mat in order to increase the comfort for the patient.

Moreover there are provided means for adjusting the height and inclination of the chair element such that the part of the body under examination is correctly positioned inside the imaging volume.

Positioning means 7 and particularly the chair element are integrated inside the magnetic structure 3 and are secured to or integrated with other covering or casing elements of the magnetic structure 3 or part thereof.

Figure 14:
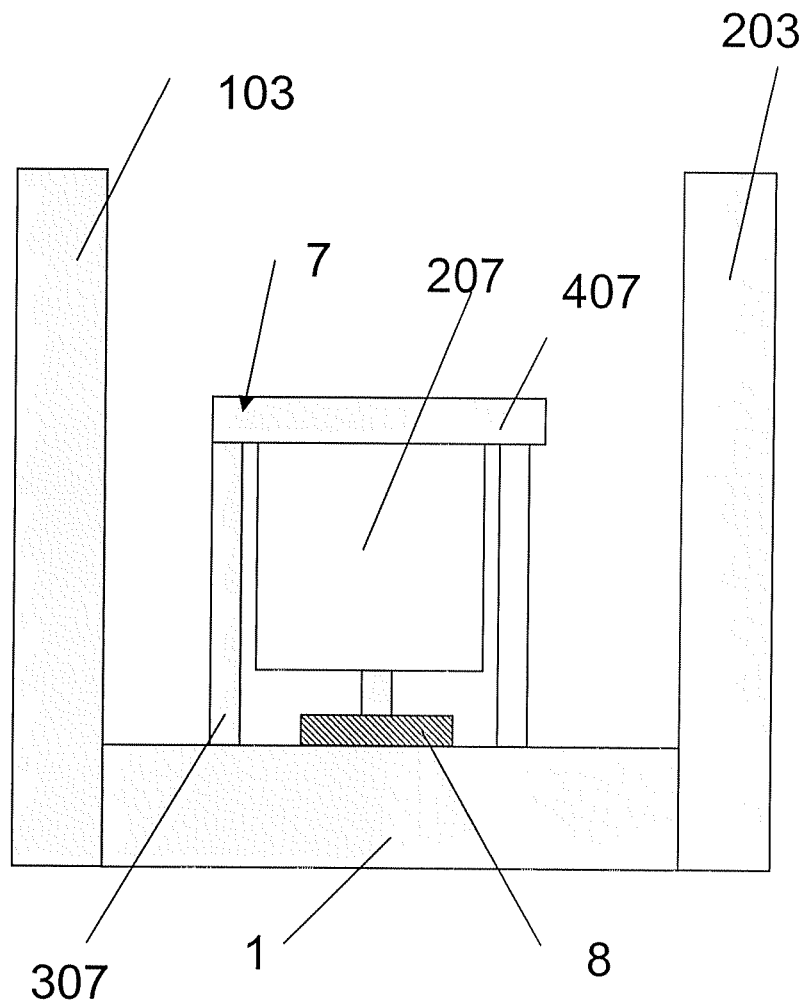
FIG. 14 is a diagrammatic front view of the MRI machine provided with a stool-like chair element.
Figure 15:
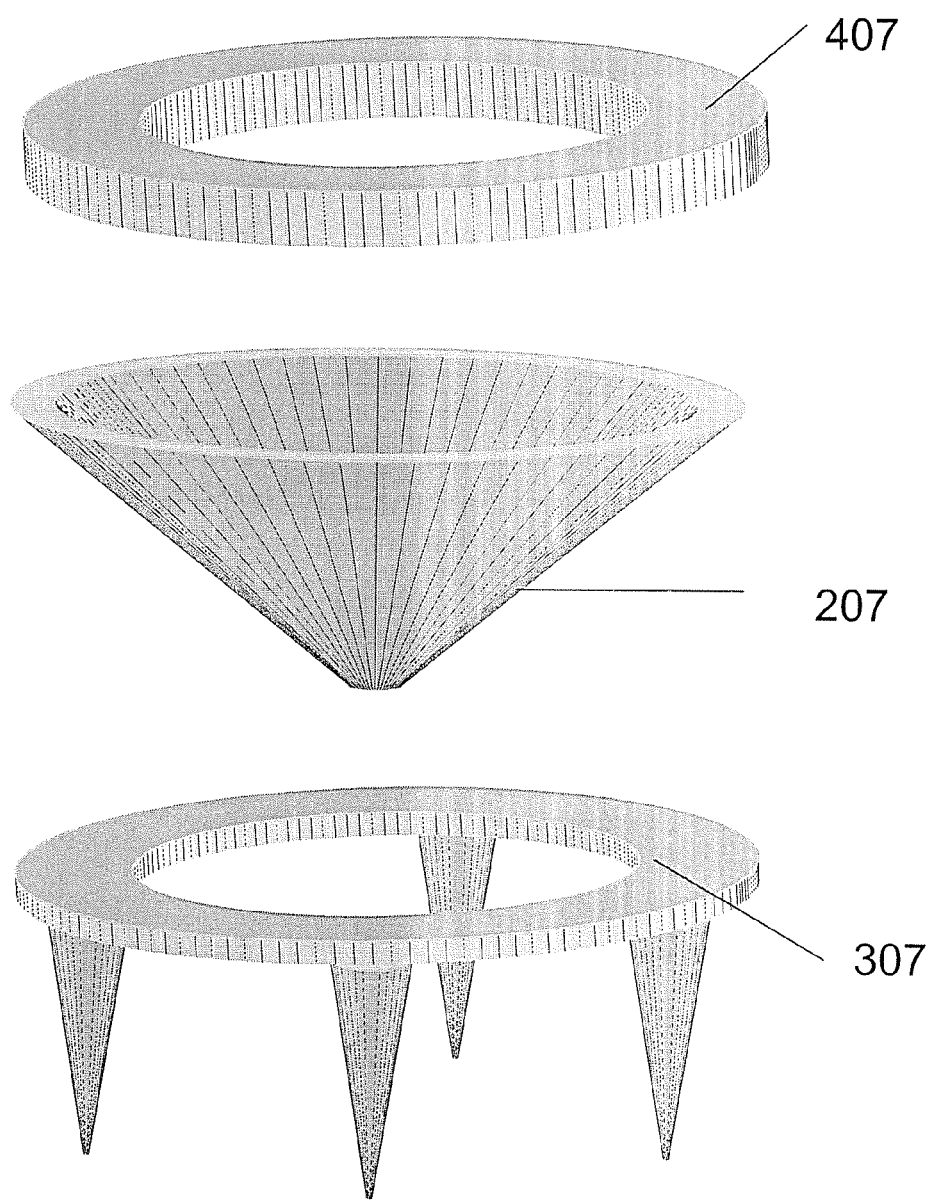
FIG. 15 is components of the stool-like chair element according to an embodiment of the present invention.

With reference to FIGS. 14, 15 on the base 1 inside the detecting cavity, a further embodiment provides the chair element to be composed of a supporting frame 307 like a stool or seat with a hole in the centre upon which a removable element is associated for collecting liquids and/or solids 207 and a resting element 407 for the patient in the seated position composed of or comprising the coil 5 receiving signals.

Means 7 for positioning the patient, particularly the toilet bowl-like chair element at the side resting on the base 1 of the MRI apparatus or supporting legs of the stool-like frame 307 with the hole can be provided with wheels allowing to take out the chair element from the magnetic structure 3.

At the feet of the patient there is provided a footboard or footrest element 8 for axially keeping the patient in the desired position inside the imaging volume during the examination. Said footrest 8 can have a fixed or adjustable height, and can be secured to the base 1 or it can be an extension of the chair element or can be a movable footrest that is brought and stopped in position after having positioned the patient.

If it is necessary to go on in acquiring images of a patient in his upright position advantageously positioning means 7 are handles, crutches or the like 9, or combinations of one or more thereof, placed inside the detecting cavity, secured to inner walls of said cavity or to the base 1 of the apparatus such that the patient is helped in maintaining the optimal position for the length of time necessary to detect images of the anatomical region of the pelvic floor, thus avoiding an excessive weariness of the back or legs. Particularly by means of said embodiment providing to keep the patient in his upright position, but also in previous embodiments wherein positioning means are composed of a chair element the at least one coil 5 receiving MRI signals is an element that can be worn with an ergonomic shape that can be adapted to the part under examination and is necessary to guarantee the acquisition of the maximum signal.

Obviously the invention is not intended to be limited as the shown and described embodiments but it can be widely changed, above all from the constructional point of view, without departing from the informing principle described above and claimed below and equivalents thereof.

The invention claimed is:

1. A method for determining information for a diagnosis of pathologic conditions of the anatomical region of the pelvic floor by MRI imaging, the method comprising:
   acquiring a sequence of MRI images along one or more predetermined section planes or inside a predetermined three-dimensional area, which planes intersect or which three-dimensional area contains at least a part of the pelvic floor;
   said image sequence being acquired for a time interval coinciding with or comprising at least a part of the length of the physiological process evacuating natural solids or liquids carried out on the basis both of a natural stimulation and an induced stimulation or during a simulation of physiological processes evacuating solids or liquids by introducing foreign bodies or substances simulating natural products;
   generating a film of the cinematographic type by using as individual frames one or more images of the sequence; and
   displaying the film for visually verifying the dynamic-morphologic behaviour of organs of the pelvic floor;
   wherein before determining or measuring dimensions or morphologic parameters of the bladder or sphincter, sequence images are subjected to a further reconstructing step by a rendering process;
   wherein, in combination with the rendering process, sequence images are subjected to a further processing process such as a morphing or a smoothing process; and
   wherein there is provided a step for verifying and correcting results of the rendering process wherein shapes or dimensions or values of dynamic deformation parameters determined by acquired images of the body under examination are compared with shapes or dimensions or values of dynamic deformation parameters determined by identical processes acquiring MRI images and processing rendering for a certain number of known clinical cases or determined on the basis of average typical values or typical value ranges provided for said shapes or dimensions or values of dynamic deformation parameters of reproduced objects and in particular of tissues or organs or structures or part thereof that are present in the region of the body under examination, a maximum differentiation threshold being established as regards increase or decrease of shapes or dimensions or values of dynamic deformation parameters determined by acquired images of the body under examination from corresponding ones relevant to known clinical cases or the ones typical for organs or tissues or structures or part thereof present in the region of the body under examination, and, when said maximum differentiation threshold is overcome, at least an error warning and a request for manually repeating the segmentation or rendering or morphing or smoothing or MRI image acquisition process being generated, or the segmentation or rendering or morphing or smoothing process being automatically repeated or a new MRI image acquisition being carried out.

2. The method according to claim 1, wherein images of the sequence or images composing the film are subjected to the following processing steps:

segmentation for indentifying subsets of pixels or voxels in images corresponding to the representation of an object or a structure provided in the three-dimensional area of which the image has been acquired or intersected by the scanning plane, identifying a real object corresponding to subsets of pixels or voxels as regards the type of tissue or organ, generating virtual objects each one corresponding to said real objects and each one composed of the subset of pixels or voxels determined by the segmentation process, for each image of the sequence subjected to previous processing steps, determining the shape or dimensions said dimensions or morphologic parameters being used as parameters for the comparison with corresponding dimensions or morphologic parameters of the same organs obtained from a database of known clinical cases.

3. The method according to claim 1, wherein the verification process or the step repeating the segmentation or rendering or morphing or smoothing or MRI image acquisition process are iteratively repeated for a predetermined number of times or until the comparison provides difference values that are below the maximum differentiation threshold.

4. The method according to claim 3, wherein, on the basis of values for said shapes or dimensions or values of dynamic deformation parameters of reproduced objects and particularly of tissues or organs or structures or part thereof that are present in the region of the body under examination determined from known clinical cases a maximum differentiation threshold value is determined for the discrimination of the presence or absence of a disease or a scale of different threshold values for determining the evolution of the disease, values for said shapes or dimensions or values of dynamic deformation parameters of reproduced objects and particularly of tissues or organs or structures or part thereof that are present in the region of the body under examination and determined from image sequences of patients under examination being compared with said threshold value discriminating the presence/absence of the disease or with said scale determining the evolution of the disease which comparison determines the indication of the probable presence/absence of the disease or the probable evolution of the disease for the specific patient.

5. The method according to claim 3, wherein for each image or image sequence a parameter measuring the average brightness or intensity is determined for the whole image or for one or more limited regions thereof that is compared with an identical reference parameter, a threshold discriminating the presence/absence of a disease or a scale of values determining the evolution of the disease being defined, from said comparison a measure of the presence/absence of the disease or the evolution degree thereof being determined.

6. The method according to claim 5, wherein the reference parameter or the discrimination threshold or the scale measuring the evolution of the disease are determined by processing data and particularly image sequences of clinical cases being part of a database of known clinical data.

7. The method according to claim 1, wherein each image or each image sequence is analysed by analysing image data relevant to a patient whose condition is not known by a process of a predictive or classification algorithm, which predictive algorithm has been subjected to training and testing by data of a database of known clinical cases.

8. The method according to claim 1, wherein parameters relevant to the presence/absence of a disease and to the evolution degree of the disease obtained by the segmentation or rendering process and by the comparison with corresponding data of the clinical database and parameters relevant to the presence/absence of the disease or the evolution degree thereof obtained by the analysis of average intensity values of image pixels or voxels or parameters relevant to the presence/absence of the disease or the evolution degree thereof obtained by the analysis of pixel by pixel or voxel by voxel with the help of predictive or classification algorithms or parameters relevant to the presence/absence of the disease or the evolution degree thereof obtained by one or more further analysis and processing processes are input variables of a final classification algorithm or of a predictive algorithm that has been subjected to training and testing on the base of a database of known clinical data and providing the final and recapitulatory indication about the probable presence/absence of diseases or the probable evolution condition thereof.

9. The method according to claim 8, wherein, in addition to data relevant to the shape or dimensions or dynamic deformation parameters, further data obtained by other diagnostic devices or personal data or data about the history of the patient are also considered.

10. The method according to claim 1, further comprising generating a database of examinations of each patient and the comparison of results of previous examinations with results of following examinations, in order to determine the evolution of the disease particularly with reference to therapy effects.

11. The method according to claim 1, wherein there is provided a step wherein shapes or dimensions or values of dynamic deformation parameters determined from acquired images of the body under examination along a time interval coinciding or comprising at least a part of the length of the physiologic process evacuating solids or liquids are compared or blended with shapes or dimension or values of static deformation parameters determined by a process of acquiring MRI images and processes carrying out the segmentation or rendering of reproduced objects and particularly tissues or organs or structures or parts thereof present in the area of the body under examination in a time interval that does not comprise the evacuation physiologic process.

* * * * *